US012310977B2

(12) United States Patent
Wiedersberg et al.

(10) Patent No.: US 12,310,977 B2
(45) Date of Patent: May 27, 2025

(54) USE OF SEMI-FLUORINATED ALKANES IN TRANSDERMAL THERAPEUTIC SYSTEMS

(71) Applicants: LTS Lohmann Therapie-Systeme AG, Andernach (DE); Novaliq GmbH, Heidelberg (DE)

(72) Inventors: Sandra Wiedersberg, Steigra (DE); Bernhard Günther, Dossenheim (DE); Dieter Scherer, Laufen (CH)

(73) Assignees: LTS Lohmann Therapie-Systeme AG, Andernach (DE); Novaliq GmbH, Heidelberg (DE)

( * ) Notice: Subject to any disclaimer, the term of this patent is extended or adjusted under 35 U.S.C. 154(b) by 235 days.

(21) Appl. No.: 15/309,595

(22) PCT Filed: May 7, 2015

(86) PCT No.: PCT/EP2015/000937
§ 371 (c)(1),
(2) Date: Nov. 8, 2016

(87) PCT Pub. No.: WO2015/172872
PCT Pub. Date: Nov. 19, 2015

(65) Prior Publication Data
US 2017/0182060 A1    Jun. 29, 2017

(30) Foreign Application Priority Data
May 13, 2014    (EP) ..................................... 14168081

(51) Int. Cl.
| A61K 31/568 | (2006.01) |
| A61K 9/70 | (2006.01) |
| A61K 31/381 | (2006.01) |
| A61K 31/485 | (2006.01) |
| A61K 31/565 | (2006.01) |
| A61K 47/06 | (2006.01) |
| A61K 47/10 | (2017.01) |
| A61K 47/24 | (2006.01) |

(52) U.S. Cl.
CPC .......... *A61K 31/568* (2013.01); *A61K 9/7084* (2013.01); *A61K 31/381* (2013.01); *A61K 31/485* (2013.01); *A61K 31/565* (2013.01); *A61K 47/06* (2013.01); *A61K 47/10* (2013.01); *A61K 47/24* (2013.01)

(58) Field of Classification Search
CPC .... A61K 31/568; A61K 9/7084; A61K 47/06; A61K 47/10; A61K 47/24
See application file for complete search history.

(56) References Cited

U.S. PATENT DOCUMENTS

| 5,152,997 | A | * | 10/1992 | Ebert | ................... | A61K 9/7084 |
| | | | | | | 424/447 |
| 5,254,338 | A | * | 10/1993 | Sakai | ................... | A61K 9/0014 |
| | | | | | | 424/443 |
| 6,262,126 | B1 | | 7/2001 | Meinert | | |
| 2012/0238639 | A1 | * | 9/2012 | Theisinger | ............. | A61K 31/05 |
| | | | | | | 514/731 |

FOREIGN PATENT DOCUMENTS

| DE | 10 2005 050 431 A2 | 4/2007 | | |
| EP | 0 670 159 A1 | 9/1995 | | |
| WO | WO 92/10231 A1 | 6/1992 | | |
| WO | WO 2002/17889 A1 | 3/2002 | | |
| WO | WO-2012160179 A2 * | 11/2012 | ........... | A61K 9/0014 |
| WO | WO 2012160180 A2 * | 11/2012 | ......... | A61K 31/4412 |

OTHER PUBLICATIONS

Minden et al., Oral ciclopirox olamine displays biological activity in a phase I study in patients with advanced hematologic malignancies. Am. J. Hematol. vol. 89, pp. 363-368 (Year: 2014).*

* cited by examiner

*Primary Examiner* — Barbara P Badio
(74) *Attorney, Agent, or Firm* — ProPat, LLC; Cathy Moore

(57) ABSTRACT

The invention relates to the use of semi-fluorinated alkanes, in particular mixed with ethanol, as solubilising agents, permeation promoters and/or enhancers for lipophilic and/or poorly skin-permeable pharmaceutical agents that are administered via a transdermal therapeutic system (TTS), and to corresponding TTSs containing such substances.

19 Claims, 2 Drawing Sheets

USE OF SEMI-FLUORINATED ALKANES IN TRANSDERMAL THERAPEUTIC SYSTEMS

CROSS-REFERENCE TO RELATED APPLICATIONS

This application is being filed under 35 U.S.C. § 371 as a National Stage Application of pending International Application No. PCT/EP2015/000937 filed May 7, 2015, which claims priority to the following parent application: European Patent Application No. 14168081.9, filed May 13, 2014. Both International Application No, PCT/EP2015/000937 and European Patent Application No. 14168081.9 are hereby incorporated by reference herein in their entirety.

FIELD OF THE INVENTION

The present invention relates to the use of semifluorinated alkanes in transdermal therapeutic systems and to transdermal therapeutic systems containing semifluorinated alkanes.

BACKGROUND OF THE INVENTION

Semifluorinated alkanes (SFAs) are known, as is their use in topically applicable pharmaceutical formulations. Here, the SFAs serve to transport active pharmaceutical ingredients into deeper skin layers and, in doing so, to overcome the outer horny layer of the skin (stratum corneum=SC) (cf. for example: EP 0670 159 A1 and WO 2012/160179 A2). The formulations are usually solutions or oily emulsions.

It has not yet been conclusively clarified as to whether the SFAs in this process primarily assume the role of solubilizers and/or of permeation-promoting substances.

However, said topically applicable pharmaceutical formulations have various disadvantages. For a start, they must generally be applied multiple times each day in order to set the therapeutically necessary concentration of the particular active ingredient at the site of action on the patient. In most cases, it is intended that topical formulations only achieve a local effect and not a systemic effect. In the case of all possible pharmaceutical forms, a necessary use which must be repeated leads in general to inadequate patient compliance.

So-called transdermal therapeutic systems (TTSs) have been proposed and developed in the prior art for the systemic administration of active pharmaceutical ingredients across the skin. TTSs are dosage forms which are applied to the skin and release an active ingredient into the skin, said active ingredient thereby being made available systemically. Such TTSs, which are also referred to as active-ingredient plasters, exist in various designs and are, for example, described in WO 02/17889 A1. But these systems too are not free of problems in their use.

Besides the outer horny layer of the skin, the active ingredient present in a TTS must first, of all also overcome various barriers within the TTS, such as, for example, a control membrane and the layer of adhesive, and, as a result, the skin flux (permeation rate in the steady state) may be ultimately reduced. However, in the case of the majority of transdermally administered active ingredients, the release from the TTS proceeds relatively rapidly and the subsequent permeation of the active, ingredient through the outermost horny layer, the actual permeation barrier of the skin, is rate-determining. Only a few active ingredients, such as, for example, nicotine, permeate the skin so well that the active-ingredient flux must be reduced with the aid of an additional membrane in the TTS in order to achieve the required blood levels.

However, the majority of transdermal active ingredients permeate the skin rather poorly and additional enhancers (permeation promoters) must be further added to the systems in order to achieve the required blood levels.

One example thereof is the administration of the lipophilic hormone testosterone (Log P=3.3). In the dissertation by Hard ling (University of Freiburg, Germany, 2008), topical formulations containing testosterone were investigated, said formulations containing SFAs as so-called carrier substances. According to the first complete paragraph on page 103 of said dissertation, an improved penetration for testosterone into the lower layers of the skin and thus also a penetration-boosting effect for the passage through the outer horny skin layer are not exhibited by said formulations.

DE 10 2005 050 431 A1 describes enhancer systems which consist of at least 4 different components and increase the permeation rate of lipophilic and/or sparingly skin-permeable active ingredients upon administration by means of TTSs. Such systems are naturally more complex than systems of simple composition.

SUMMARY OF ADVANTAGEOUS EMBODIMENTS OF THE INVENTION

It was therefore an object of the present invention to provide pharmaceutical preparations or means which do not have the disadvantages described for the prior art or which have said disadvantages at least to a distinctly lower extent. Furthermore, it is intended that corresponding pharmaceutical preparations be as easy-to-use and easy-to-manage as possible for patients.

DETAILED DESCRIPTION OF ADVANTAGEOUS EMBODIMENTS OF THE INVENTION

Figure 1:
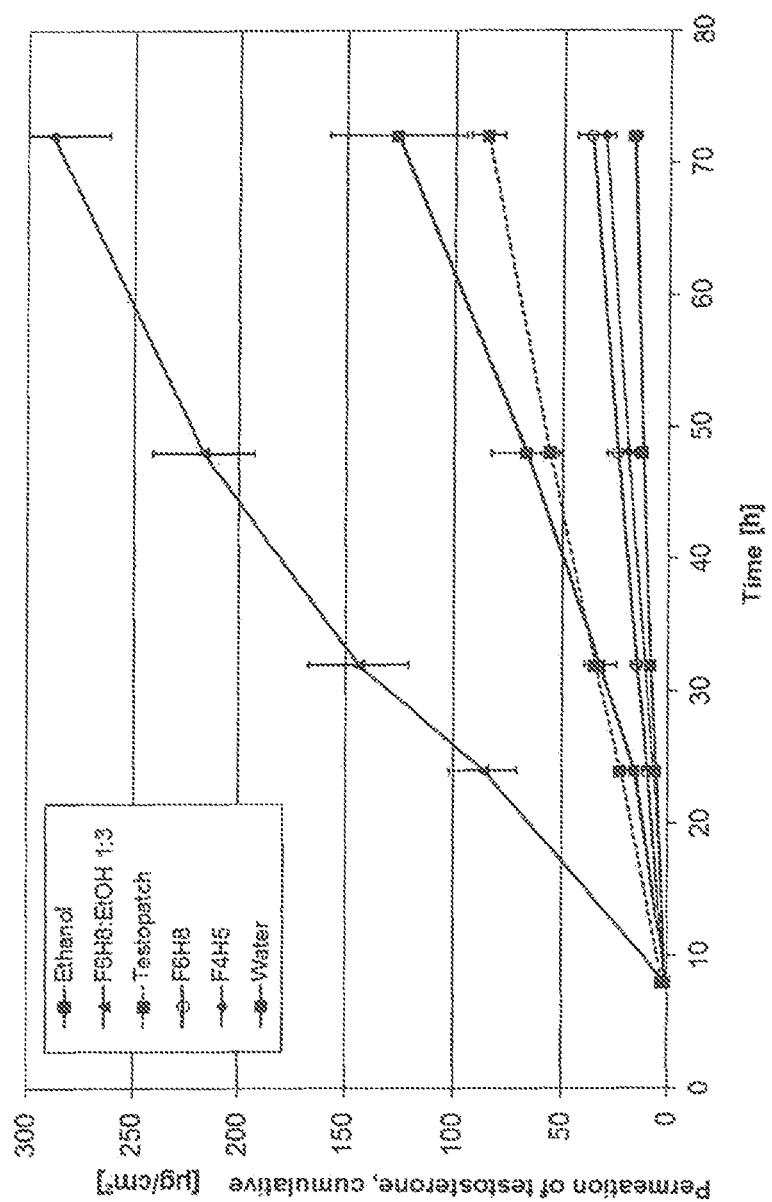
FIG. 1 is a graphical illustration of the cumulative permeation rates for testosterone solutions in the solvents of Table 1.

The object according to the invention is achieved by the use of SFAs as solubilizer and/or permeation-promoting substance and/or as enhancer in TTSs.

Semifluorinated alkanes (SFAs) are linear or branched alkanes in which the hydrogen atoms have been replaced in part with fluorine. In one form preferred for the purpose of the present invention, said SFAs consist of a nonfluorinated part and a perfluorinated part. Perfluorinated means that, in this part of the molecule, all hydrogen atoms have been replaced with fluorine. A simple labeling of such SFAs is possible by nomenclature in the form of the abbreviations FnHm and FnHmFo, where: F=perfluorinated segment/part, H=nonfluorinated segment/part of the SFA and n, m and o are independently the number of carbon atoms in the particular segment. Thus, the abbreviation F3H3, for example, means 1-perfluoropropylpropane since the linear SFAs are preferred, and F3H3 could also mean 2-perfluoropropylpropane, 1-perfluoroisopropylpropane or 2-perfluoroisopropylpropane, this would be additionally separately noted in the last-mentioned cases. Without these indications, the abbreviations FnHm and FnHmFo therefore mean linear SFAs. This means that F6H8 means per fluorohexyloctane and F4H5 means perfluorobutylpentane.

Preferably, n, m, o are independently 3-20 carbon atoms; more particularly, the perfluorinated segment of the SFA has 4-12 carbon atoms and/or the nonfluorinated segment has 4-10 carbon atoms. Preferred compounds are therefore F4H5, F4H6, F4H8, F6H4, F6H6, F6H8 and F6H10. Particular preference is given to F4H5, F4H6, F6H6 and F6H8 and especially F6H8 and F4H5 thereof, with regard to the characterization of the SFAs according to the invention, express reference is made to WO 2012/160179 A2 (pages 5 and 6).

The SFAs used according to the invention can also be mixtures of various representatives of SFAs. Preferably, these in turn contain at least one of the abovementioned substances.

Furthermore, it has been found that the addition of monohydric and polyhydric alcohols, such as, for example, ethanol, 1,2-propanediol and the various butanediols, can distinctly increase the solubilizing and permeation-promoting properties of the SPAs or of the SFA mixtures. Preference is given here especially to ethanol, which can exhibit distinct effects even in small amounts. This so-called enhancer effect or boost effect is particularly high for SFA/ethanol mixtures. Preferably, the mixture ratio of SFA(s) or SFA mixtures to alcohol is from 1:5 to 5:1, more particularly from 1:3 to 3:1. Volume fractions are concerned here in each case.

According to the invention, the stated substances and substance mixtures are preferably utilized for supplying especially more lipophilic and/or sparingly skin-permeable substances to a patient by means of TTSs across the skin.

"Lipophilic" in the context of the present description means that the active ingredient has a great desire to pass into a phase immiscible with water. Lipophilic substances are distinguished by a high Log P value (log P>2.5). The Log P value is the partition coefficient of a substance between octanol and water: $C_{octanol}/C_{water}$ In the context of the present description, "poorly water-soluble" is understood to mean active ingredients which have a solubility of less than 0.3% by weight in water, i.e., substances of which less than 3 mg are soluble in one milliliter of water.

"Sparingly skin-permeable" in the context of the present description refers to active ingredients, the flux of which is by itself, i.e., in the absence of permeation boosters or other measures for increasing skin penetration, too low in order to be able to achieve the plasma concentration of active ingredient that is required to achieve a therapeutic effect.

In general, active ingredients having a molecular weight of >500 or a Log P of less than 1 or more than 3 are considered sparingly skin-permeable.

Lipophilic, poorly water-soluble active ingredients are generally distinguished by a poor bioavailability in the case of oral administration. Although a transdermal administration of active ingredients which are poorly bioavailable in the case of oral administration is conceivable in principle, excessively lipophilic active ingredients are usually also counted among the sparingly or poorly skin-permeable active ingredients.

Examples of lipophilic active pharmaceutical ingredients preferred in this context are testosterone (Log P=3.3), estradiol (log P=4.01), buprenorphine (log P=4.98), rotigotine (log P=4.58), oxybutynin (log P=4.02) and other hormones.

According to the prior art, TTSs consist of a pharmaceutical-impermeable support layer (also called backing layer), a pharmaceutical-containing reservoir layer, and a layer of adhesive for fastening on the skin. The last-mentioned layer can also be identical to the pharmaceutical-containing layer. Moreover, TTSs generally have a protective layer which is likewise active-ingredient-impermeable and is to be removed prior to application. In addition, yet further components can be present, such as, for example, a control membrane limiting the release of active ingredient.

The TTSs according to the invention can be prepared both in the form of matrix systems and in the form of reservoir systems (reservoir matrix TTSs, liquid reservoir systems) or membrane systems.

A matrix system, for example in the form of a monolithic matrix TTS, fundamentally consists of a protective backing layer, an active-ingredient-containing adhesive matrix and a removable protective film. A reservoir matrix TTS generally has a backing layer, a liquid reservoir, a control membrane, an adhesive layer and a removable protective film. The components of a modified TTS for volatile active ingredients consist of backing layer, adhesive layer, active-ingredient-containing nonwoven, adhesive layer and removable protective film. Such systems are known to a person skilled in the art and described, for example, in DE 10 2005 050 431 A1 and WO 02/17889 A1.

The so-called reservoir or liquid reservoir systems are preferred for the purpose of administering highly volatile active ingredients or additives (e.g., enhancers). In the case of said systems, a drying process in which the active ingredient or excipient might be volatilized is not necessary. Transdermal therapeutic liquid reservoir systems per se, in which a generally liquid active-ingredient preparation (as solution, emulsion, suspension) is present in a pouch formed from a release-controlling membrane and a preferably active-ingredient-impermeable film, are known to a person skilled in the art. In the case of said systems, pharmaceutically acceptable and skin-compatible organic solvents serve as carrier medium, the viscosity of which can be adjusted to the particular technological requirements using suitable excipients (e.g., mineral oils). Ideally, the solvents used have, at the same time, properties promoting the permeation of the active ingredient through the skin of the patient. However, it is also possible to add substances promoting the permeation of the active ingredient, so-called enhancers, to the solvent. Furthermore, the liquid reservoir systems comprise a layer of adhesive, by means of which the system is fastened on the skin of the patient.

In the case of the liquid reservoir system according to the invention, the active ingredient is in dissolved, dispersed, suspended or emulsified form in the SFA(s), the SFA mixtures or the mixtures of one or more SFAs with one or more further alcohols.

The fraction of active ingredient in the active-ingredient-containing preparation is from 0.1 to 50% by weight, preferably from 5 to 25% by weight. Furthermore, the active-ingredient preparation can contain further substances by means of which the release of the active ingredient—in the sense of a delayed release—can be controlled. Such substances are, for example, absorption agents.

The absorption agents can be selected from the group comprising cyclodextrins, polyvinylpyrrolidones and cellulose derivatives.

The active-ingredient preparation can additionally contain viscosity-increasing excipients which do not have any release-controlling function. Preferably, the viscosity-increasing excipient is selected from the group consisting of finely dispersed silicon dioxide, for example AEROSIL R 974® (Silica Dimethyl Silylate), polyacrylic acids, for example CARBOPOL 934P polyethylene glycols. An example of a preferred polyethylene glycol is CARBOWAX 1000® (Polyehtylene Glycol 1000). The active-ingredient preparation in the liquid reservoir can be in the form of a solution, dispersion, suspension, paste or gel.

In the case of the TTS according to the invention, the release of the active ingredient and of the enhancer (SFAs and the mixtures thereof) from the liquid reservoir system into the skin can be controlled via:

The skin as permeation barrier,
the type of control membrane used, for example in terms of the chemical composition thereof and/or the pore size;
the type of layer of adhesive that is used under the control membrane, which layer is used to fasten the system on the skin, for example in terms of the chemical composition and/or layer thickness thereof;
a delayed release through the use of absorption agents in the liquid reservoir, for example cyclodextrins, polyvinylpyrrolidones or cellulose derivatives.

As control membrane, it is possible to use microporous polymer films produced with defined pore size and composed of polypropylene, polyurethane, copolymers of ethylene and vinyl acetate and silicones. Said polymer films are suitable provided that they are resistant to the substances present in the active-ingredient preparation.

As adhesives which have properties controlling the release of the active pharmaceutical ingredient and which are attached under the control membrane for fastening of the system on the skin, preference is given to adhesives based on copolymers of ethylene and vinyl acetate, in combination with adhesive resins as additives. In the case of said adhesives, it is possible to adjust the penetrability or permeability of the layer of adhesive via the ratio of ethylene to vinyl acetate. Preference is also given to adhesives based on silicones, since they are permeable for the majority of active ingredients and excipients, and to adhesives based on poly(meth)acrylates and adhesives based on polyisobutylenes.

The present invention therefore comprises
a) the use of SFAs or mixtures of SFAs or mixtures of SFAs with alcohols in TTSs, wherein they can act as solubilizer, permeation promoter and/or enhancer,
b) TTSs containing the substances mentioned under a),
c) TTSs containing the substances mentioned under a) and an active pharmaceutical ingredient which is preferably lipophilic and/or is sparingly skin-permeable, and
d) the use of the TTSs mentioned under b) and c) for applying active pharmaceutical ingredients across the (human) skin.

The following exemplary embodiments serve to further elucidate the invention, without said invention being restricted thereto. On the contrary, all the stated features are freely combinable in any form which appears appropriate for a person skilled in the art, and all of said forms are encompassed by the present invention.

Examples 1 and 2

The adhesive liquid reservoir systems are prepared by an active-ingredient-free polyacrylate adhesive solution of the type DURO TAK® 1050 (from National Starch, Antwerp) or a copolymer of ethylene and vinyl acetate with an addition of an adhesive resin based on rosin (FORAL® 85 B) being firstly coated on a siliconized polyethylene terephthalate film in a wet-layer thickness of 300 μm with the aid of an extension knife. Thereafter, the solvents are removed by drying the coated film at 50° C. for 30 min in a drying cabinet with an exhaust air system. The solvent-free and active-ingredient-free adhesive film is then covered with a 35 μm thick polyurethane film (OPRAFLEX®, from Lohmann) or a polypropylene film as later control membrane by lamination. A polyester film (SCOTCHPAK® No. 1220, from 3M) is applied to the control membrane and sealed using a specific sealing mask heated via a commercially available iron to form pouches having a round reservoir with a diameter of 25 mm.

Via an existing opening to the reservoir, the particular mixture according to Tables 1 and 2 is filled into the reservoir by means of a syringe. After filling of the reservoir, the fill opening is heat-sealed with the aid of an iron, forming a completely self-contained and storage-stable liquid reservoir system.

The permeation rates of the aforementioned systems are determined on the "human epidermis" in vitro diffusion model with the aid of modified Franz diffusion cells. In all cases, the acceptor medium used is phosphate buffer (pH 5.5) with an addition of 0.1% $NaN_3$ as preservative, thermostatically controlled to 32° C.

Figure 2:
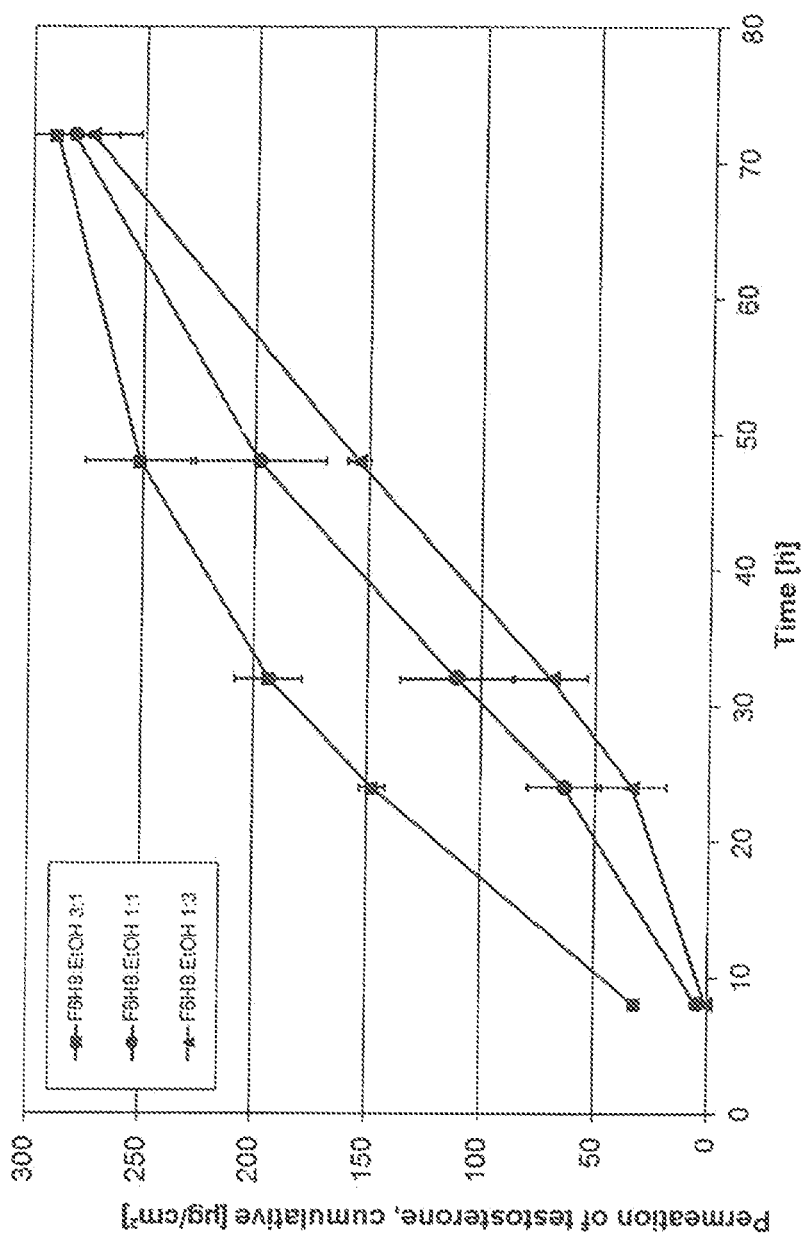
FIG. 2 is a graphical illustration of the cumulative permeation rates for testosterone solutions in the solvents of Table 2.

The cumulative permeation rates of testosterone are depicted in FIGS. 1 and 2, with the individual measurement points representing the mean value of three individual measurements. The results of the investigations on the permeation of testosterone are compiled in Tables 1 and 2.

TABLE 1

(Permeation of testosterone, saturated solution):

| Vehicle | Saturation solubility $c_S$ [mg/ml] | $J_{SS}$ [μg/cm$^2$h] | Enhance factor |
|---|---|---|---|
| Water | 0.02 | 0.2 | Reference |
| F6H8 | 0.15 | 0.6 | 3.0 |
| F4H5 | 0.42 | 0.5 | 2.5 |
| Ethanol | 106.9 | 2.0 | 10.0 |
| Testopatch | 0.5 mg/cm$^2$ | 1.3 | 6.5 |
| F6H8:ethanol 1:3 (V/V) | 80.37 | 5.5 | 27.5 |

TABLE 2

(Permeation of testosterone; solution with 80% of the saturation concentration):

| Vehicle | Concentration c [mg/ml] | $J_{SS}$ [μg/cm$^2$h] | Enhance factor |
|---|---|---|---|
| F6H8:ethanol 3:1 (V/V) | 23.1 (80% cs) | 6.8 | 34.0 |
| F6H8:ethanol 1:1 (V/V) | 42.6 (80% cs) | 5.6 | 28.0 |
| F6H8:ethanol 1:3 (V/V) | 60.7 (80% cs) | 5.0 | 25.0 |

FIG. 1 shows the cumulative permeation rates in [μg/cm$^2$] for a saturated solution of testosterone in the solvents (media or vehicles) according to the corresponding Table 1. The highest cumulative permeation rates naturally also lead to the highest in vitro skin flux $J_{ss}$ in [μg/cm$^2$×h] according to Table 1. Here, the system composed of SFA and alcohol (F6H8:ethanol 1:3 (V/V)) exhibits an exceptional enhancer effect, which can also be referred to as a synergistic effect (with respect to water, this effect is a factor of EF=28).

FIG. 2 and the corresponding Table 2 exhibit said enhancer effect of a mixture of SFA and alcohol (here using the example of F6H8 and ethanol) for various volume mixture ratios (V/V) of the components using the example of a testosterone solution having 80% of the particular saturation concentration. The results show an unexpected enhancer effect (in comparison with water as solvent) for all mixture ratios and around a factor of EF=34 for a mixture of 3 volume fractions F6H8 and one volume fraction ethanol.

The invention claimed is:

1. A transdermal therapeutic system (TTS) for systemic administration of active pharmaceutical ingredients across human skin, said TTS comprising systemically active pharmaceutical ingredient(s) in combination with a permeation promoter,
said permeation promoter comprising one or more semifluorinated alkanes (SFAs) and a monohydric or polyhydric alcohol; and
wherein the systemically active ingredient is lipophilic and/or sparingly skin-permeable,
the TTS comprises adhesive that fastens the system to skin and controls the release of the systemically active pharmaceutical ingredient, said adhesive formed from polymer consisting of an adhesive resin based on rosin in combination with (a) ethylene-vinyl-acetate-copolymer-based adhesive, (b) silicone-based adhesive, (c) poly(meth)acrylate-based adhesive, or (d) polyisobutylene-based adhesive.

2. The TTS as claimed in claim 1, wherein the systemically-active pharmaceutical ingredient(s) is/are in dissolved, suspended or emulsified form in an SFA or in a mixture of multiple SFAs.

3. The TTS as claimed in claim 1, wherein the SFAs are linear alkanes of the general formula FnHm, where F is a perfluorinated segment of the molecule, H is a nonfluorinated segment of the molecule and n and m are independently the number of carbon atoms in the particular segment.

4. The TTS as claimed in claim 3, wherein n=4-12 and m=4-10.

5. The TTS as claimed in claim 3, wherein FnHm is F4H5, F4H6, F4H8, F6H4, F6H6, F6H8 or F6H10.

6. The TTS as claimed in claim 1, wherein the alcohol is a monohydric alcohol.

7. The TTS as claimed in claim 6, wherein the alcohol is ethanol.

8. The TTS as claimed in any of claim 1, wherein the volume ratio of SFA or SFAs to alcohol is from 5:1 to 1:5.

9. The TTS as claimed in claim 1, wherein the systemically active ingredient is present at a fraction ranging from 0.1-50% by weight.

10. The TTS as claimed in claim 1, wherein the TTS is a reservoir or liquid reservoir system.

11. A method of administering a TTS comprising SFA or SFAs in a mixture with monohydric or polyhydric alcohols as solubilizer, permeation promoter and/or enhancer for active pharmaceutical ingredients.

12. The method as claimed in claim 11, wherein a mixture of one or more SFAs with ethanol is used.

13. The TTS as claimed in claim 1, wherein the TTS is a matrix system comprising a backing layer, a systemically-active-ingredient-containing adhesive matrix and a removable protective film.

14. The TTS as claimed in claim 1, wherein the systemically active ingredient is testosterone, estradiol, buprenorphine, rotigotine, oxybutynin or hormone other than testosterone or estradiol.

15. The TTS as claimed in claim 14, wherein the systemically active ingredient is testosterone, the SFA is F6H8, the alcohol is ethanol and said TTS exhibits a skin flux ranging from 5.0 to 6.8 ($\mu$g/cm$^2$ h), said skin flux being higher than a comparable TTS containing either F6H8 or ethanol alone.

16. A transdermal therapeutic system (TTS) for systemic administration of active pharmaceutical ingredients across human skin, said TTS comprising systemically active pharmaceutical ingredient(s) in combination with a permeation promoter, said permeation promoter comprising
one or more semifluorinated alkanes (SFAs) and a monohydric or polyhydric alcohol,
wherein the volume ratio of SFA or SFAs to alcohol is from 5:1 to 1:3;
the systemically active ingredient is a lipophilic and/or sparingly skin-permeable active ingredient;
the systemically active ingredient is a hormone, and
the TTS comprises adhesive that fastens the system to skin and controls the release of the systemically active pharmaceutical ingredient, said adhesive formed from polymer consisting of an adhesive resin based on rosin in combination with (a) ethylene-vinyl-acetate-copolymer-based adhesive, (b) silicone-based adhesive, (c) poly(meth)acrylate-based adhesive, or (d) polyisobutylene-based adhesive.

17. The TTS as claimed in claim 16, wherein the systemically active ingredient is testosterone and the volume ratio of SFA or SFAs to alcohol is from 1:1 to 5:1.

18. The TTS as claimed in claim 1, wherein the TTS comprises testosterone as the systemically active ingredient and further includes a release-controlling membrane.

19. The TTS as claimed in claim 1, wherein the adhesive that fastens the system to skin and controls the release of the systemically active pharmaceutical ingredient consists of an adhesive resin based on rosin in combination with either ethylene-vinyl-acetate-copolymer-based adhesive.

* * * * *